United States Patent [19]

Anderson et al.

[11] 4,157,871

[45] Jun. 12, 1979

[54] SYSTEM FOR RATE IMMUNONEPHELOMETRIC ANALYSIS

[75] Inventors: Robert J. Anderson, Orange; Robert M. Studholme, Tustin, both of Calif.

[73] Assignee: Beckman Instruments, Inc., Fullerton, Calif.

[21] Appl. No.: 796,621

[22] Filed: May 16, 1977

Related U.S. Application Data

[63] Continuation-in-part of Ser. No. 692,089, Jun. 2, 1976, abandoned.

[51] Int. Cl.² .................... G01N 21/00; G01N 31/00
[52] U.S. Cl. .................................. 356/341; 23/230 B; 356/338
[58] Field of Search ............... 356/103, 104, 201, 204, 356/180; 23/230 B

[56] References Cited

U.S. PATENT DOCUMENTS

| | | | |
|---|---|---|---|
| 3,725,204 | 4/1973 | Marshall | 356/103 |
| 3,730,842 | 5/1973 | Wyatt | 356/103 |
| 3,748,044 | 7/1973 | Liston | 356/180 |
| 3,832,532 | 8/1974 | Praglin | 356/103 |
| 3,905,767 | 9/1975 | Morris | 356/103 |
| 3,967,901 | 7/1976 | Rodriguez | 356/103 |
| 3,990,851 | 11/1976 | Gross | 356/103 |
| 4,063,817 | 12/1977 | Shimamura | 356/180 |

Primary Examiner—Samuel W. Engle
Assistant Examiner—Donald P. Walsh
Attorney, Agent, or Firm—R. J. Steinmeyer; Robert R. Meads

[57] ABSTRACT

A system for the detection of precipitate-forming antigens by means of the reaction with their corresponding antibodies is disclosed. The reaction of precipitate-forming antigens with their respective antibodies produces a precipitate in proportion to either the antibody concentration or the antigen concentration, depending on which is present in excess. The method does not require formation of actual precipitate, but measures the formation of "scattering centers" — i.e., molecular aggregates of sufficient size to produce measurable scatter of light. The quantity of scattering centers formed is measured by nephelometric means and the measuring system performs an immunonephelometric analysis. In particular, the rate of change of the nephelometric signal with respect to time is measured and the peak rate and time to the peak rate established. From these simultaneous measurements both the antigen/antibody concentration and the condition of antibody or antigen excess are determined.

19 Claims, 21 Drawing Figures

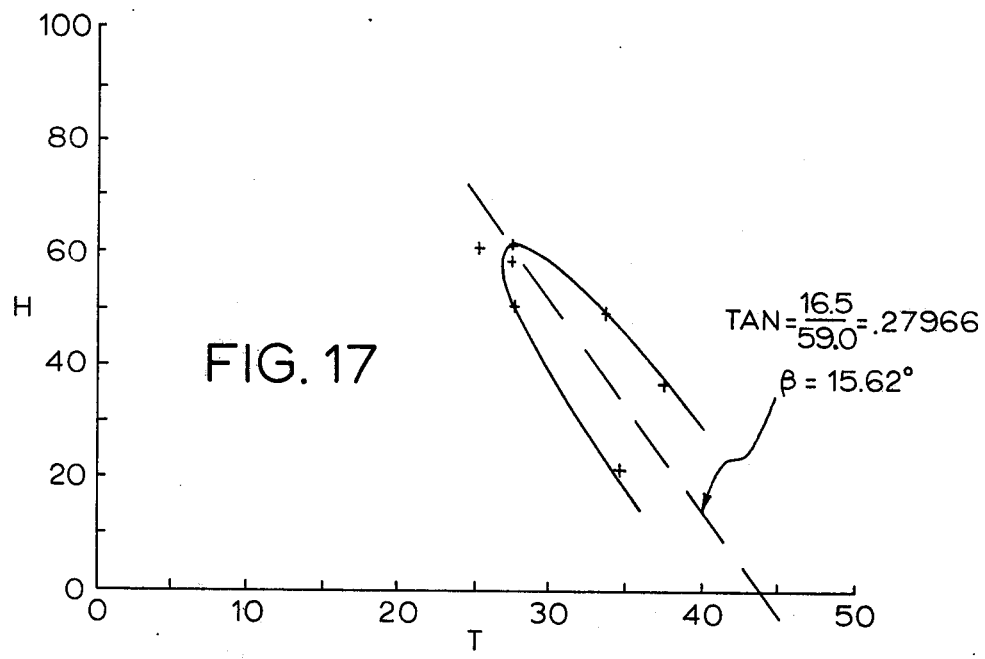
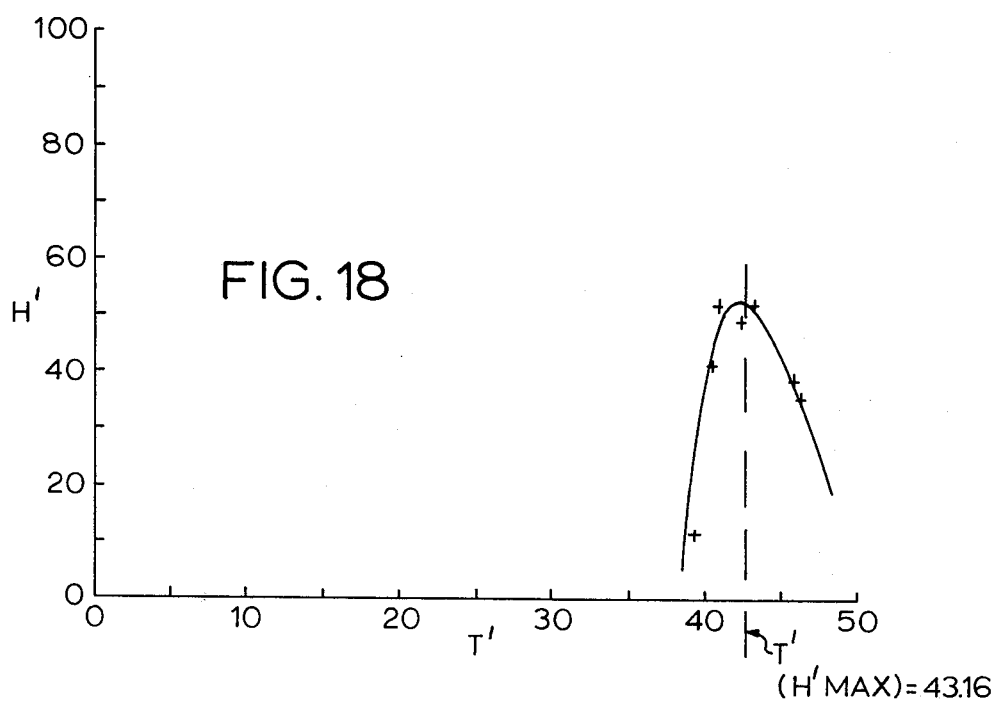

SYSTEM FOR RATE IMMUNONEPHELOMETRIC ANALYSIS

CROSS REFERENCE TO RELATED APPLICATION

This is a continuation in part of U.S. patent application Ser. No. 692,089 filed June 2, 1976, now abandoned.

BACKGROUND OF THE INVENTION

The present invention relates to the determination of concentration of antibodies or precipitate-forming antigens present in a wide variety of samples, and more particularly, to such determination by nephelometric means.

Specific antigens may be detected by means of their reaction with corresponding antibodies. For example, polyvalent protein antigens may react with their respective antibodies to produce a precipitate which forms in such a way that the amount of precipitate is proportional to either the antibody concentration or the antigen concentration, depending on which is present in excess. Such antibodies are called "precipitins", and their reactions are "immuno-precipitin reactions". As stated, in these reactions, the amount of precipitate is proportional to either the antibody concentration or the antigen concentration, depending on which is present in excess, as shown in FIG. 1. For example, if the antibody is present in excess, the quantity of precipitate formed is related to the concentration of antigen in the sample. On the other hand, if excess antigen is present, the quantity of precipitate is related to the concentration of antibody. For purposes of discussing the prior art and background of the invention and, later, for setting forth the present invention, the analysis of antigen in sera during antibody excess will be used. It is to be understood that this convention is adopted for ease of discussion and is not intended to limit the scope of the invention as set forth herein.

The combination of antigen with antibody is a specific yet reversible chemical reaction. Since its discovery, the precipitin reaction has been used extensively as a qualitative or semi-quantitative technique for estimating either antigen or antibody concentrations. Generally, this is accomplished by allowing the reaction to go to completion and centrifuging or filtering the precipitate formed. Under optimal conditions, the reaction occurs rather rapidly, and precipitation may be complete within a time period of only a few minutes. Under more typical conditions, the precipitation requires intervals of as long as several hours, or even a number of days, depending on other solution characteristics such as ionic strength, salt species present, and the presence of other hydrophobic or hydrophilic macro-molecules.

When the reaction is allowed to go to completion, the amount of protein precipitated for a given amount of antibody increases with the amount of polyvalent antigen up to a maximum, beyond which larger amounts of the antigen lead to progressively less precipitation. Thus the quantity of precipitate formed in an antigen-antibody reaction depends on the relative concentrations of the two reactants. The curve of FIG. 1 describes the quantity of precipitate formed, as a function of the antigen concentration in the reaction mixture, for a given antibody concentration. It may be seen that there are three distinct zones in the curve of antigen concentration versus quantity of precipitate formed. On the ascending limb of the curve, the antibody is present in excess. On the descending limb of the curve, the antigen species is present in excess. The region of maximum precipitation is called the equivalence point with matching concentrations of antigen and antibody.

Most antibody molecules are bivalent, while the precipitating antigens are multivalent. These reactants combine in a series of consecutive reactions which may be summarized in the following steps:

(1) Primary interaction of association, with formation of a binary antigen-antibody complex;
(2) Lattice formation through reaction of the primary complexes leading to the formation of larger complexes consisting of a lattice of antigen and antibody molecules;
(3) Aggregation of these lattice-like complexes to form the visible precipitate.

The specific structure of the stable lattice achieved with the bivalent antibody and multivalent antigen is still unknown, since the number of possibilities is large. There is, however, significant evidence for the formation of a stable lattice, and it is apparent that in the antibody excess region of the precipitin curve there is no free antigen detectable in the soluble phase after formation of the precipitate, although antibody is still present in the supernatant liquid. In the equivalence region, neither antigen nor antibody is found in the supernatant liquid, except perhaps in very small amount.

In the area of antigen excess, complex formation itself is a much simpler process. In this region little precipitation occurs because of the high probability that each antibody molecule will be bound to two antigen molecules, with subsequent lattice formation being impossible owing to the lack of free antibody valence. Precipitation, then, may be considered a consequence of the growth of antibody-antigen aggregates in such a way that each antigen molecule is linked to more than one antibody molecule, and, in turn, each antibody molecule is linked to more than one antigen molecule. When these aggregates exceed some critical volume they settle out of solution spontaneously due to the increase in sedimentation rate caused by the increase in the volume of the particle. Thus, if the lattice formed in Step 2 of the aforementioned mechanism is sufficiently large, as will tend to be the case near equivalence, precipitation will occur without the aggregation of adjacent lattices.

On the other hand, under conditions of antibody excess, the close packing of antibody molecules when bound to an antigen molecule provides opportunity for neighboring antibody molecules to react with one another through the formation of ionic bonds between oppositely charged groups. As a consequence, lattices consisting of large numbers of antibody molecules may become relatively hydrophobic and tend progressively to associate with one another and become increasingly insoluble. Thus in the condition of extreme antibody excess, corresponding to very low antigen concentrations, even though sufficiently large lattices to form precipitation may not occur, aggregation of small hydrophobic lattice elements consisting of low concentrations of antigen still give rise to a visible precipitate. This view is supported by an analysis of the effects of ionic strength on precipitation and by experiments concerning the advancement of precipitation. In the former, increasing salt concentrations cause increasing precipitation. In the latter, the addition of hydrophilic agents or species were found to increase the effective hydrophobicity of the precipitating species. Thus, it may be seen that at a very low antigen concentration a visible precipitate may be formed through the third step, but not through the second step, in the aforementioned mechanism. Accordingly, at such low antigen concentrations, the relationship between quantity of precipitate formed and concentration of the antigen molecule is extremely nonlinear.

Once a precipitin curve has been constructed for a known antibody and its respective antigen, the antiserum can be used to measure the concentration of that antigen in an unknown sample. The assay for antigen is carried out in the antibody excess region (except for that very low antigen concentration region discussed above), since that is the region where precipitation is quantitatively related to the amount of antigen. Throughout the range from an antigen concentration of zero up to the equivalence point, all of the available antigen in the unknown sera will be complexed by the excess antibody and will be precipitated, making the precipitin reaction an extremely good quantitative tool. In fact, extreme specificity is provided if the antiserum is free of extraneous antibodies that could precipitate with other antigens in the test sample solution. Quantification of antigens in this way is ambiguous, however, since a given quantity of precipitate may imply one value of antigen concentration if the antibody is present in excess, while it may imply another value of antigen concentration if the antigen is present in excess. That is to say, a given amount of precipitate formed in an antibody/antigen reaction may correspond to two values of antigen concentration, depending on which of the two species, antibody or antigen, is present in excess. With unknown samples, the latter fact is often in question.

Methodologies presently exist for quantifying precipitate-forming antigens or antibodies in solution by analyzing precipitates formed upon their reaction with their specific immunochemical partners. Most commonly, the amount of precipitate formed is measured by measuring the amount of light scattered from a beam of light passing through the solution. In general, the procedure involves the addition of the antigen containing sample to an antibody solution and a buffer. The solution is then allowed to incubate over the period of time necessary for the antigen and antibody to react completely. Upon complete reaction, the solution is placed in a measuring cell. A beam of collimated light then is passed through the cell and the amount of light scattered perpendicularly to the direction of the incident light is measured to produce a "nephelometric signal". By graphic analysis using a series of standard curves, the value of the nephelometric signal is converted to a measure of antigen concentration in the sample solution. In this regard, the standard curves are developed by graphically plotting the value of nephelometric signals generated from reactions of standard antigen solutions of various dilutions (in saline) with reagents of known antibody concentrations. The graphic analysis involves operating with the standard curve derived under the same antigen, dilution, and reagent concentration conditions as those under which a sample solution was tested to generate the nephelometric signal. Specifically, the value of the nephelometric signal is graphically noted on the abscissa for the selected standard curve and a corresponding value noted for antigen concentration on the ordinate for the selected standard curve. The noted value of antigen concentration is the concentration of antigen in the sample solution if the sample has been measured under conditions of antibody excess as previously described.

Nephelometric methods afford a convenient means for monitoring immuno-precipitin reactions at an early stage in the reaction. As the reaction proceeds, the initial 1:1 complexes grow to form larger units which increasingly scatter light prior to the separation of a precipitate. Given sufficient time, particles large enough to precipitate will be formed. Significantly increased light scattering is observed, however, before the larger units become sufficiently agglomerated to settle out. Thus, the term "scattering centers" rather than "particles" or "precipitate" is more accurately used to describe the product measured by nephelometric techniques.

The formation of the larger complexes in a free solution medium can be accelerated by the presence of hydrophilic agents which tie up a significant fraction of the water, thus enhancing the probability of protein-protein interaction. The most widely used of these hydrophilic agents is polyethyleneglycol (PEG) with an average molecular weight of 6000. In the presence of about 40 g/1 PEG 6000, the build-up of complexes of sufficient size to give a level of light-scatter adequate for quantitative measurement occurs in a time interval of tens of seconds, and the maximum scatter level is reached within a few minutes, as opposed to 30-90 minutes in the absence of PEG. The short reaction time obtained in the presence of PEG makes possible the rapid direct measurement of precipitating antigens, by means of measuring the increase of light scattered by the larger units formed from the primary antigen-antibody complexes.

The nephelometric approach, as contrasted to procedures in which the precipitate is physically separated from the clear solution for measurement, affords a means for observing the immuno-precipitin reaction under dynamic conditions -- i.e., while it is taking place. The initial 1:1 complexes generally are too small to scatter visible light to a significantly greater extent than do the separated components. Thus, only the secondary build-up of larger units which serve as scattering centers can be observed. However, the actual end point of an immuno-precipitin reaction is difficult to define. This is because the precipitate formed eventually tends to settle out from the solution thereby decreasing the light scatter at a time when scatter should otherwise be maximal. The observed scatter is thus dependent both on the amount of material and on the state of its dispersion within the measuring cell. It is therefore preferable to make nephelometric measurements under dynamic conditions, rather than waiting for the reaction to go to completion.

Instead of waiting for the reaction to be complete before measuring the nephelometric signal, the nephelometric signal can be measured beginning at the time when the antigen and the antibody are brought into contact in solution. In such case, it is found that the nephelometric signal develops to its final value over a period of time which may be as short as a few minutes or as long as several hours. During the development of the reaction, the nephelometric signal takes the form of a sigmoidal curve, beginning at some relatively low value, progressively increasing at an accelerating rate until at some point in time it undergoes an inflection and begins to decrease its time rate of change until the nephelometric signal asympotitically approaches its final value, as shown in FIG. 2. The first derivative of the nephelometric signal as a function of time is therefore roughly Gaussian in shape, as shown in FIG. 3. It develops a peak value at the inflection point, after which the increasing nephelometric signal begins to approach its asymptotic value. It has been determined that the time rate of change of the nephelometric signal at the inflection point is directly related to the final asymptotic value of the nephelometric signal. It is possible, therefore, to quantify the amount of immuno-precipitin reaction, by measuring the derivative of the nephelometric signal with respect to time, and quantifying the peak of the rate signal thus obtained. Under suitable conditions, a maximum or "peak" rate is obtained within 10-40 seconds after introduction of the triggering reagent (antigen or antibody) to the reaction mixture.

The rate of change of the nephelometric signal has been proposed in the quantification of specific protein antigens in sera as set forth in the following publications: (1) Specific Protein Analysis by Light-Scatter Measurement with a Miniature Centrifugal Fast Analyzer, T. O. Tiffany, J. M. Parella, W. F. Johnson, and C. A. Burtis, *Clinical Chemistry*, Vol. 20, No. 8 (1974), p. 1055; (2) Kinetics of the IgG Anti-IgG Reaction, as Evaluated by Conventional and Stopped-Flow Nephelometry, John Savory, Gregory Buffone, and Richard Reich, *Clinical Chemistry*, Vol. 20, No. 8 (1974), p. 1071; (3) Use of a Laser-Equipped Centrifugal Analyzer for Kinetic Measurement of Serum IgG, Gregory J. Buffone, John Savory, and R. E. Cross, *Clinical Chemistry*, Vol. 20, No. 10 (1974), p. 1320; and (4) Evaluation of Kinetic Light Scattering as an Approach to the Measurement of Specific Proteins with the Centrifugal Analyzer. I. Methodology, Gregory J. Buffone, John Savory, R. E. Cross, and J. E. Hammond, *Clinical Chemistry*, Vol. 21, No. 12 (1974) p. 1731.

When considering the prior art, however, it is important to ascertain the way in which the particular authors are using the term "rate". In particular, the term "rate" is often used in place of intensity when referring to the nephelometric signal. In that regard, the instantaneous rate of production of precipitate is directly related to the quantity of precipitate and, therefore, the intensity of the nephelometric signal. Such uses of the term "rate" to indicate intensity are common in publications (2), (3) and (4) above. For example, in publication (2) at page 1074, FIG. 7 is titled "Rate of change of light scattering in polyethylene glycol". Inspection of the Figure, however, discloses a coordinate system labeled "relative intensity" and "time" while the curve itself is the classic sigmoidal curve characteristic of the nephelometric intensity signal. By contrast, publication (1) uses rate in its proper manner, being the rate of change with respect to time of the nephelometric signal. It is in this manner that the term "rate" is used hereinafter to describe a novel approach to the determination of antibody/antigen excess in immunonephelometric analysis. The lack of such an improved method of determining antibody/antigen excess is noted in reference (2) wherein it states, "Detection of antigen excess is also an important factor in all immunoassay methods. Possibly a centrifugal analyzer system could be used to monitor early changes in reaction rates and provide a means by which low antigen concentration could be differentiated from very high antigen concentrations as seen in FIG. 4. " The detection of antigen excess and the equilibrium area is an even more serious problem as this is the environment of actual interest in immunoassay procedures as will be discussed in greater detail hereinafter. As will be seen, in simple excess situations as opposed to "high" excess situations an improved method of determining antibody/antigen excess is required before true rate analysis of a nephelometric signal can be usefully employed in the determination of protein concentrations. The present invention provides such an improved method and apparatus.

Previously, the rate of change of a nephelometric signal has been determined by a periodic sampling of the nephelometric signal. In particular, maximum change during such sampling periods has been determined by a sample and comparison method and, when found, the maximum value and next lower value have been used to calculate a slope or rate line directly related to the final protein concentration. The accuracy of such an approach is, of course, dependent on the sampling frequency. The shorter the period, the higher the probability that the sample will be taken during the period that the time rate of change of the nephelometric signal reaches a maximum. Under such circumstances, a reasonably accurate approximation of the maximum or peak rate probably will be obtained. However, when dealing with probabilities, there is also a considerable chance of error and incorrect determinations of final protein concentration. Further, such presently employed methods provide only an approximation of the elapsed time to the occurrence of peak rate and hence are rather inaccurate in their determination of antigen excess. Accordingly, even having determined peak rate, the present methods are inaccurate in determining which of the two possible concentration values it represents.

Therefore, it is the object of the present invention to provide a technique for establishing both concentration and antigen excess existence following a determination of the precise maximum rate and the exact time of occurrence of that maximum rate.

SUMMARY

The present invention discloses methods and apparatus for the determination of concentration and antibody/antigen excess in precipitin-forming immunochemical reactions by using nephelometric techniques. In particular, the derivative of the nephelometric signal caused by light scatter from the scattering centers in the antigen/antibody reaction is monitored to establish the precise peak rate and the exact time to that peak rate. From this single point identification both concentration and antibody/antigen excess are determined.

In particular, the objects of the invention are accomplished by apparatus comprising: a cell for holding a sample containing a precipitin-forming antigen or antibody, means for producing and directing a light beam into a sample in the cell, photodetector means for detecting scattered light from the sample and for producing a signal indicative of the quantity thereof, first signal differentiator means connected to said photodetector means for producing a first rate signal indicative of the rate of change with respect to time of the quantity of scattered light, first peak rate detector means connected to the first signal differentiator means for detecting a maximum value of the first rate signal, and, trigger means for producing a start signal upon initiation of an immunochemical reaction in the cell. Employing the foregoing apparatus, a method is disclosed wherein antigen/antibody excess is determined in immunonephelometric analysis by the steps of: passing a beam of light through a sample cell wherein the antigen/antibody reaction is taking place, sensing the start of the reaction, measuring the intensity of a nephelometric signal produced by the light beam scattering from an antigen/antibody precipitate forming from the reaction, producing a first time derivative signal from the nephelometric signal, detecting a maximum value H of the first derivative signal, and, comparing a function f(H) of the maximum value H graphable on a first coordinate system to a first threshold value whereby if the f(H) is on one side of the first threshold value antigen excess is determined and if the f(H) is on the other side of the first threshold value antibody excess is determined.

DESCRIPTION OF THE DRAWINGS

FIG. 17 is a graph of the form of FIG. 11 for the specific case of human serum immunoglobulin G (IgG) diluted 1:8 in a buffer solution of 0.1 M NaCl+3% PEG.

FIG. 18 is a graph of the form of FIG. 13 derived from FIG. 17.

DESCRIPTION OF THE PREFERRED EMBODIMENT

Figure 1:
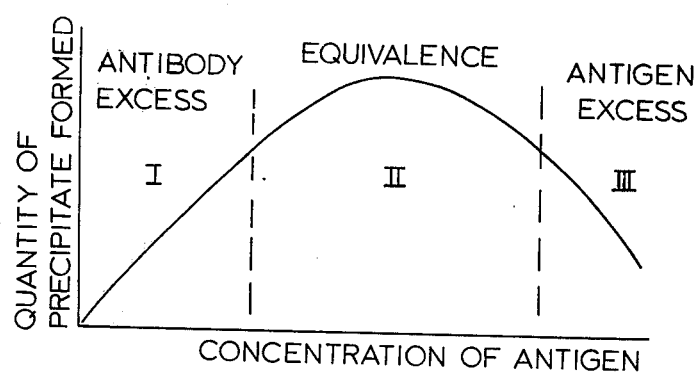
FIG. 1 is a graph of quantity of precipitate formed as a function of the concentration of antigen and showing regions of antibody excess, equivalence, and antigen excess.

The formation of aggregates of sufficient size to scatter light by means of an antigen-antibody reaction may be approximated by a series of second-order steps of the form $$Ab + Ag \rightarrow AbAg$$

$$AbAg + AbAg \rightarrow (AbAg)_2$$

$$(AbAg)_2 + AbAg \rightarrow \ldots$$

As a first approximation, however, the second-order chain reaction steps occurring after the initial formation of the binary complex may be lumped together to yield a model of the form $$Ab + Ag \xrightarrow{k_1} AbAg \tag{1}$$

$$AbAg \xrightarrow{k_2} P \tag{2}$$

where P represents the scattering product, $K_1$ is a second-order rate constant, and $k_2$ is a pseudo-first-order rate constant.

The differential rate equations based on this simplistic mechanism are then of the form $$d[Ab]/dt = -k_1[Ab][Ag] = d[Ag]/dt \tag{3}$$

$$d[AbAg]/dt = k_1[Ab][Ag] - k_2[AbAg] \tag{4}$$

$$d[P]/dt = k_2[AbAg] \tag{5}$$

Considering the system to be in moderate antibody excess, the concentration of antibody, [Ab], is a constant and integration of (3) yields for the antigen concentration $$[Ag] = [Ag]_o e^{-k_1' t} \quad (6)$$

where $K_1'$ is now a first-order rate constant containing both $k_1$ and the antibody concentration, [Ab]. Thus the antigen concentration undergoes an exponential decrease with time, starting at its initial value, $[Ag]_o$.

The concentration of antigen-antibody complex, [AgAb], is obtained by assuming that its concentration at time $t=o$ is zero, thus $$[AbAg] = \frac{[Ag]_o k_1'}{(k_2 - k_1')} e^{-k_1' t} - e^{-k_2 t} \quad (7)$$

and the concentration of the complex is seen to begin at zero, increase to a maximum, and then decrease to a concentration of zero after a long time.

Now, since stoichoimetry requires that the three rate expressions, equations (3)–(5), sum to zero, that is $$d[Ag]/dt + d[AbAg]/dt + d[P]/dt = 0 \quad (8)$$

we can immediately obtain the concentration of scattering product [P], as $$[P] = [Ag]_o 1 + \frac{1}{(k_1' - k_2)} k_2 e^{-k_1' t} - k_1' e^{-k_2 t} \quad (9)$$

which is the characteristic sigmoidal curve obtained in the measurement of scattered light from precipitin reactions.

Of greater interest, however, is the rate expression for the formation of the scattering product, which is obtained from equation (5) as $$d[P]/dt = [Ag]_o \frac{k_1' k_2}{k_2 - k_1'} e^{-k_1' t} - e^{-k_2 t} \quad (10)$$

Figure 2:
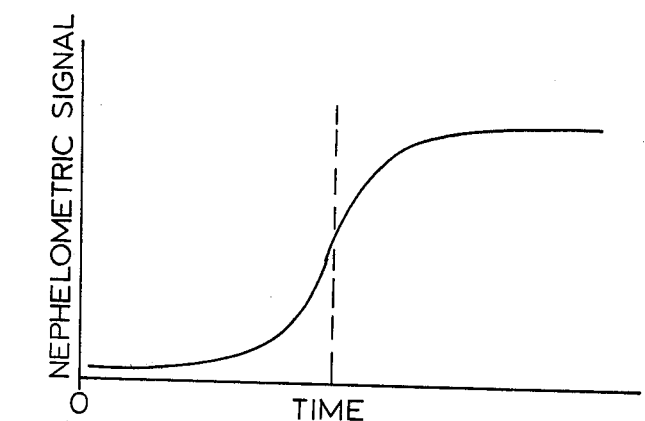
FIG. 2 is a graph of the nephelometric signal during antigen/antibody quantification and excess determination, as a function of time.
Figure 3:
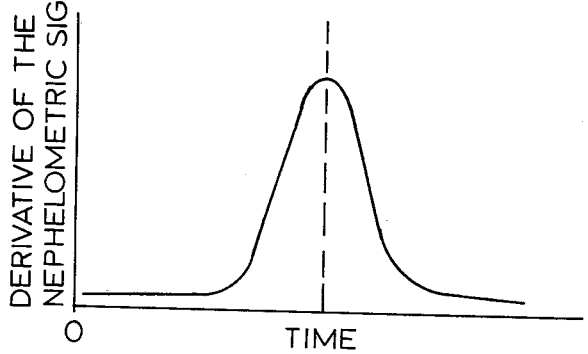
FIG. 3 is a graph of the rate of change or derivative of the nephelometric signal during antigen/antibody quantification and excess determination, as a function of time.

Thus the formation of product is slow at first, during the "induction" period. The duration of the induction period, taken as the time to reach the inflection point on the [P] versus t curve is easily seen to be the time for [AbAg] to reach its maximum value, since when $d^2[P]/dt^2 = 0$, $d[AbAg]/dt = 0$ from equation (5). It is essential to note, moreover, that the rate curve amplitude is a function of the initial concentration of antigen, $[Ag]_o$. Moreover, the peak rate is given by $$(d[P]/dt_{max}) = [Ag]_o \frac{k_1' k_2}{k_2 - k_1'} \frac{k_2 - k_1'}{k_2} e^{-k_1' t_{max}} \quad (11)$$

$$(d[P]/dt_{max}) = [Ag]_o k_1' e^{-k_1' t_{max}} \quad (12)$$

where $t_{max}$ is the time at which the peak rate occurs. Thus the peak rate is seen to be proportional to the initial antigen concentration, as is observed experimentally to a first approximation. FIG. 2 is a plot of the concentrations of antigen, [Ag], antigen-antibody complex, [AbAg], and product, [P], as obtained from equations (6), (7), and (9). It can be seen from FIGS. 2 and 3 taken together, that the peak rate, which is proportional to the concentrations of antigen-antibody complex, [AbAg], occurs at the inflection point of the product concentration curve.

The foregoing treatment provides only an approximate representation of the behavior of this complex reaction system. Thus the maximum rate, under conditions of moderate antibody excess, shows an approximately linear increase with antigen concentration. The actual dependence in extreme antibody excess is more nearly quadratic, however. This is because the simplification of equation (2) does not hold under these conditions, where the mechanism of buildup of scattering centers requires hydrophobic interactions of smaller lattices. This simplified treatment cannot treat the regions near equivalence or in antigen excess, where the assumption of constant antibody concentration no longer applies.

The present invention is based on the principle that the maximum or peak rate of change in a nephelometric signal generated by the scatter of light from a precipitin-forming antigen-antibody reaction is directly proportional to the final nephelometric signal over some reasonable range of antigen concentrations, and more importantly, that the peak rate monotonically increases with and is approximately linearly proportional to antigen concentration over some range of concentrations. In fact, in such range, Rate$_{max}$=K[Ag], where K is a constant and [Ag] is the concentration of antigen. It has been found further that the exact time at which the peak rate of change in the nephelometric signal occurs after the initiation of reaction of the antigen and antibody solutions is indicative of which of the two reaction constituents is present in excess. That is to say, the antigen excess situation can be distinguished from the antibody excess situation by observing characteristics of the data such as the exact time after the start of the reaction at which the peak rate occurs. Thus, a single simultaneous measurement of peak rate, and time from initiation of the reaction to occurrence of that peak rate, can yield both a value for the antigen concentration and an indication of whether that value corresponds to an antigen excess or an antibody excess situation, thereby removing the ambiguity caused by the precipitin curve shown in FIG. 1.

The advantages attendant to the present invention are obvious. First, the determination is rapid, being completed in a time typically less than 60 seconds. This compares with endpoint determinations which require times ranging from several minutes to as long as several hours. Second, an unequivocal determination is provided in which the antibody excess situation can be easily discriminated from the antigen excess situation. Also, since the determination is rapid, it may be done in a discrete cell or cup as opposed to being performed in a flow system or a batch system that allows for incubation of the sample. Thus, a rate method for determining specific precipitin-forming antigen is provided by the present invention which is simple, accurate, and rapid.

Figure 4:
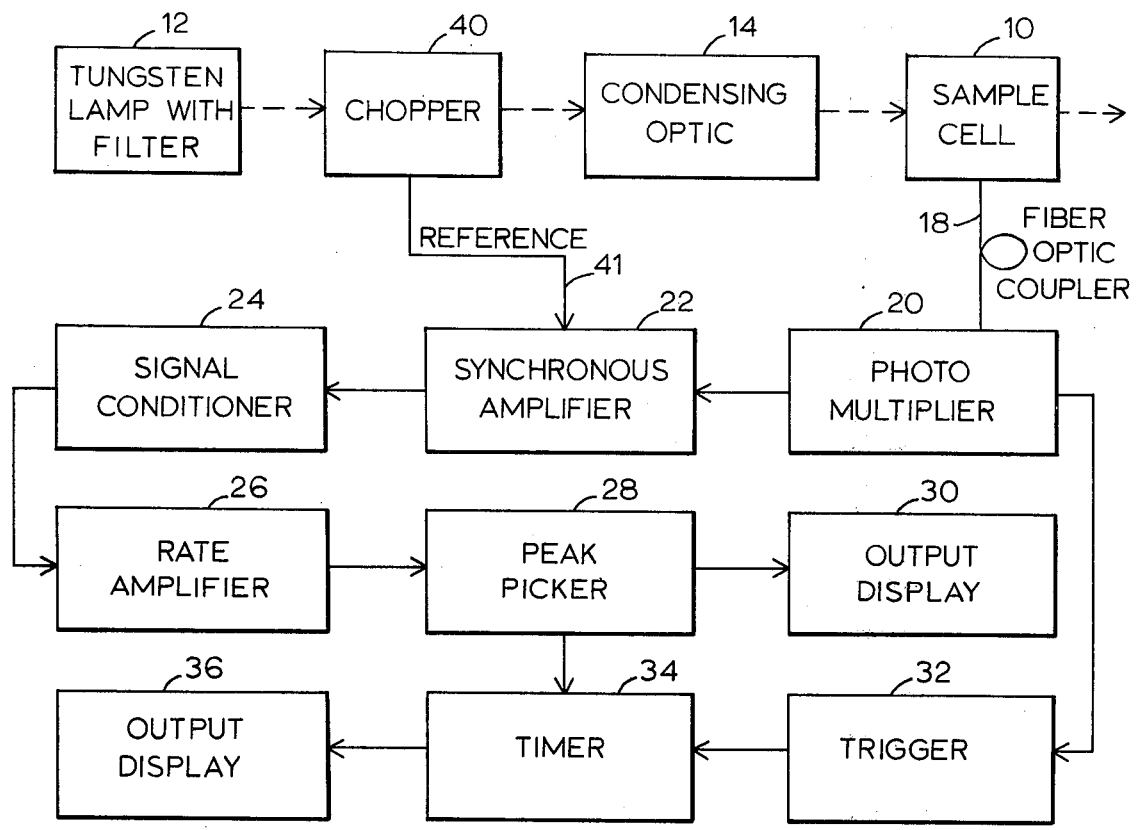
FIG. 4 is a block diagram of preferred apparatus employed to practice the method of the present invention for antigen/antibody quantification and excess determination.

Referring to FIG. 4, a block diagram of a system for practicing the present invention is shown. In FIG. 4, the optical paths are shown by dashed line arrows and the electrical paths are shown in solid line arrows. Generally speaking, the system employs a sample cell or cup 10. A light source 12 is provided in conjunction with optical apparatus 14 for passing a well defined beam of light 16 through the sample cell or cup 10. A fiber optic probe 18 or other light gathering optical means for observing the scattered light at some angle removed from the path of the light through the sample is connected to cup 10. Buffer solutions and any other necessary standard ingredients in the reaction, with the exception of the sample, may be automatically supplied to the reaction cell or cup 10 if desired by means of a pump (not shown) or the like, while the cell may be automatically drained in like manner by means of a second pump (also not shown). The antigen sample to be quantized (or its corresponding antibody, if such is the desired approach) is injected into cell 10 to begin the reaction with the balance of the solution which has been previously pumped into cell 10 in pre-established measured amounts. A photomultiplier 20 is connected to the opposite end of probe 18 for detecting the scattered light and generating an electrical signal (nephelometric signal) proportional thereto. A synchronous amplifier 22 is connected to photomultiplier 20 for amplifying the nephelometric signal. The amplified nephelometric signal is then applied to a signal conditioning means 24 which removes any portion of the signal caused by light scatter not directly related to the formation of the scattering centers from the antibody-antigen reaction (hereinafter referred to as noise). The conditioned nephelometric signal is then input to a rate amplifier 26 which outputs a signal which is the time rate of change of the nephelometric signal. The output of rate amplifier 26 is connected to a peak-rate picker 28 which monitors the rate signal from rate amplifier 26 for its maximum or peak value, which it then saves. A display 30 connected to the peak rate picker 28 indicates the measured peak rate and may comprise a conventional digital panel meter. In addition, the system includes a trigger 32 for accurate detection of the initiation of the reaction. The trigger 32 controls the operation of a timer 34 for measuring the elapsed time between the initiation of the reaction and the occurrence of the peak rate as indicated by an input from the peak rate picker 28. A second display 36 is connected to timer 34 and displays the elapsed time.

Figure 5:
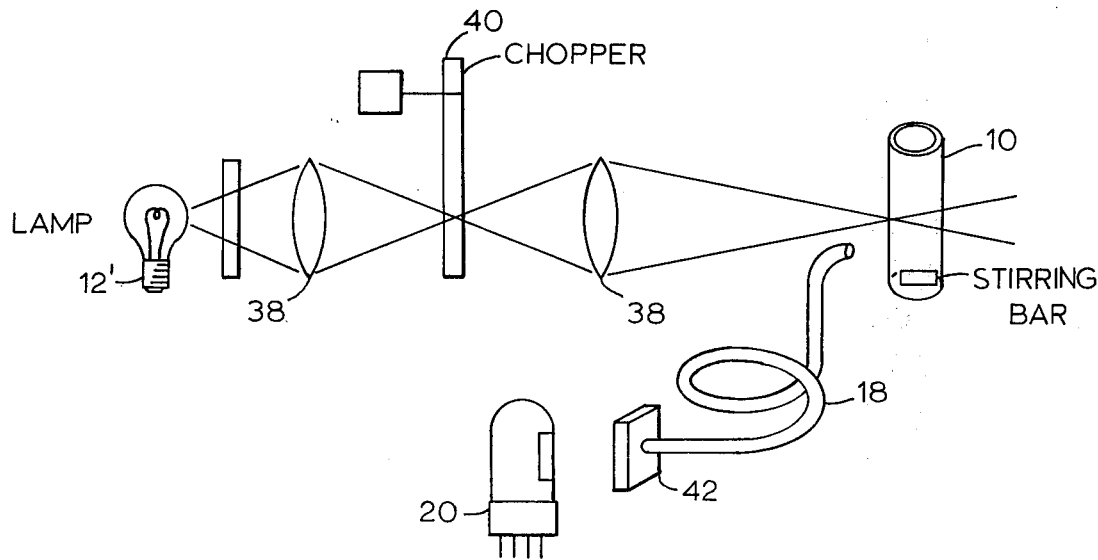
FIG. 5 is a simplified drawing of the optical system employed in the apparatus of FIG. 4.

The optical portion of the system is shown in greater detail in FIG. 5 as comprising a tungsten lamp 12', a series of condensing lenses 38, and an optical chopper 40 all of conventional design. The chopper 40 operates at the same reference frequency as the synchronous amplifier 22 and, in combination therewith, produces a rejection of outside light interference. The beam of light 16 generated by the lamp 12' and lenses 38 may be passed through the measuring cell 10 via a pair of aligned openings or windows in opposite side walls of the cell 10. Upon striking the scattering centers formed by the antibody-antigen reaction within the cell 10, light is scattered and is preferably detected by means of a fiber optic coupler 18' inserted in the cell at an angle removed from the path of the incident light through the cell.

The angle at which the scattered light is observed by the fiber optic coupler 18' should be an optimal angle chosen to maximize the signal-to-noise ratio. The preferred angle depends on the configuration of the cell 10 and must be independently established for each different cell configuration to maximize the signal-to-noise ratio. In this regard, the signal is the nephelometric signal obtained by means of the scattering of light from the scattering centers formed in the reaction. The noise is the signal generated in the photomultiplier 20 by light which is scattered by the walls of the cell 10, or light from other sources of stray light in the system. A second consideration that should be made in choosing an "optimal" angle for detecting the scattered light is the fact that the rate of the nephelometric signal (from scattered light entering optic coupler 18) varies as a function of the angle of the optic coupler into cell 10 (observation angle) due to the change in particle size as a function of time during the immunoprecipitin reaction.

As noted, the preferred light source 12 is a tungsten lamp 12'. As shown in FIG. 5, it is used in conjunction with a broad band filter 42 to select the wavelength region from 400 to 500 nanometers, as opposed to a single wavelength source such as a helium neon laser. While the latter may be used, the tungsten lamp 12' is preferred because observation over a broad wavelength band is superior in this case to observation at a single wavelength. In particular, particle sizes change radically during the formation of the precipitate, with the result that the particulate scattering function at a single wavelength may change erratically while the average particle scattering function over a range of wavelengths remains relatively constant. Thus, the nephelometric signal from a broad wavelength band of light tends to be less noisy and more stable than that from a single wavelength light source such as that provided by a small laser.

It is also preferred that the scattering light be of shorter wavelengths such as those in the blue and green regions of the spectrum since the magnitude or strength of the light scattering off the scattering centers increases as the fourth power of the frequency of the illuminating light source. Using the shorter wavelengths of higher frequency thus permits the use of less sensitive and, therefore, less expensive photomultipliers.

As previously stated, detection of the scattered light is provided by means of the photomultiplier tube 20 connected to the fiber optic coupler 18' observing the scattered light at an angle removed from the path of the light beam 16. The photomultiplier 20 converts the optical signal observed by the coupler 18' into an electronic signal which is then amplified by means of the synchronous amplifier 22 as illustrated in FIG. 4. The synchronous amplifier 22 is of conventional design and responds only to signals of the same phase as the chopper 40. As shown, a reference connection 41 exists between the chopper 40 and the synchronous amplifier 22 to assure that synchronous amplifier is "on" only when chopper 40 is allowing light to pass through cell 10. Synchronous amplifier 22 thus only responds to light signals occurring at a frequency identical to that at which chopper 40 is chopping the light through cell 10. This technique is well known in the art and forms no part of the present invention. The chopping in conjunction with the synchronous amplifier 22 separates the desired signal from noise caused by room light or other extraneous sources of light. This is particularly important in allowing the use of the present invention in a lighted laboratory without requiring the addition of cumbersome and expensive light interlocks into the cell.

Figure 6:
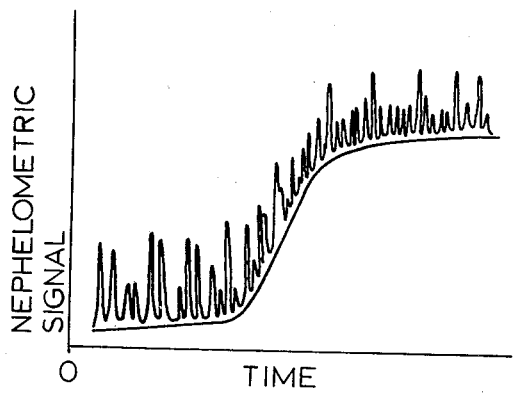
FIG. 6 is the graph of FIG. 2 showing unipolar noise superimposed on the nephelometric signal during antigen/antibody quantification and excess determination.

The predominant source of noise in the system is scattering from species other than the scattering centers of the immunoprecipitin reaction (for example, dust or air bubbles in the sample cell). In this regard, it has been found that the signal coming from the amplifier 22 consists of the desired nephelometric signal with a series of unipolar noise spikes superimposed on top of it as depicted in FIG. 6. Since such extraneous scattering particles in the cell tend to increase the magnitude of the nephelometric signal, it is desirable to remove their effect rather than integrate to obtain an average over some period of time. This is most easily accomplished in the present case by a "bottom follower". In other words, since the noise is on top of the signal, the bottom of the signal curve or the continuously instantaneously lowest value of the nephelometric signal is the nephelometric signal from cell 10. Thus, the electronic system of the present invention preferably contains the signal conditioner 24 functioning in a manner as a "bottom follower" to remove the noise spikes due to the presence of dust or air bubbles in the sample and to transmit only that portion of the electronic signal due to light scattered by the antibody/antigen precipitate. It has been found that, contrary to the usual procedure, it is desirable to continually stir the solution in cell 10 as with a magnetic stirring bar during the entire reaction period at least up to the time of detection of the peak rate. By stirring the solution, the air bubbles, etc., are moved about such that their presence produces only a series of sharp spikes which are easily removed by the signal conditioner 24 to produce a more accurate signal of interest.

Again referring to FIG. 4, the conditioned nephelometric signal is continuously differentiated in the rate amplifier 26 to provide a rate signal output which is a measure of the rate of change of the nephelometric signal with respect to time and hence the concentration of the antigen in accordance with the formula $Rate_{max} = K[Ag]$. (If antibody were being quantized this would be, of course, $Rate_{max} = K'[Ab]$.) In this regard, the rate amplifier is of conventional design and applies the rate signal to the peak picker 28, also of conventional design. The peak picker 28 functions to select the maximum or peak rate of the rate signal and to hold a signal having a value proportional thereto for use by a computer or display on the digital panel meter. In addition, the peak picker 28 operates in response to the detection of the peak rate to stop the timer 34.

Figure 21:
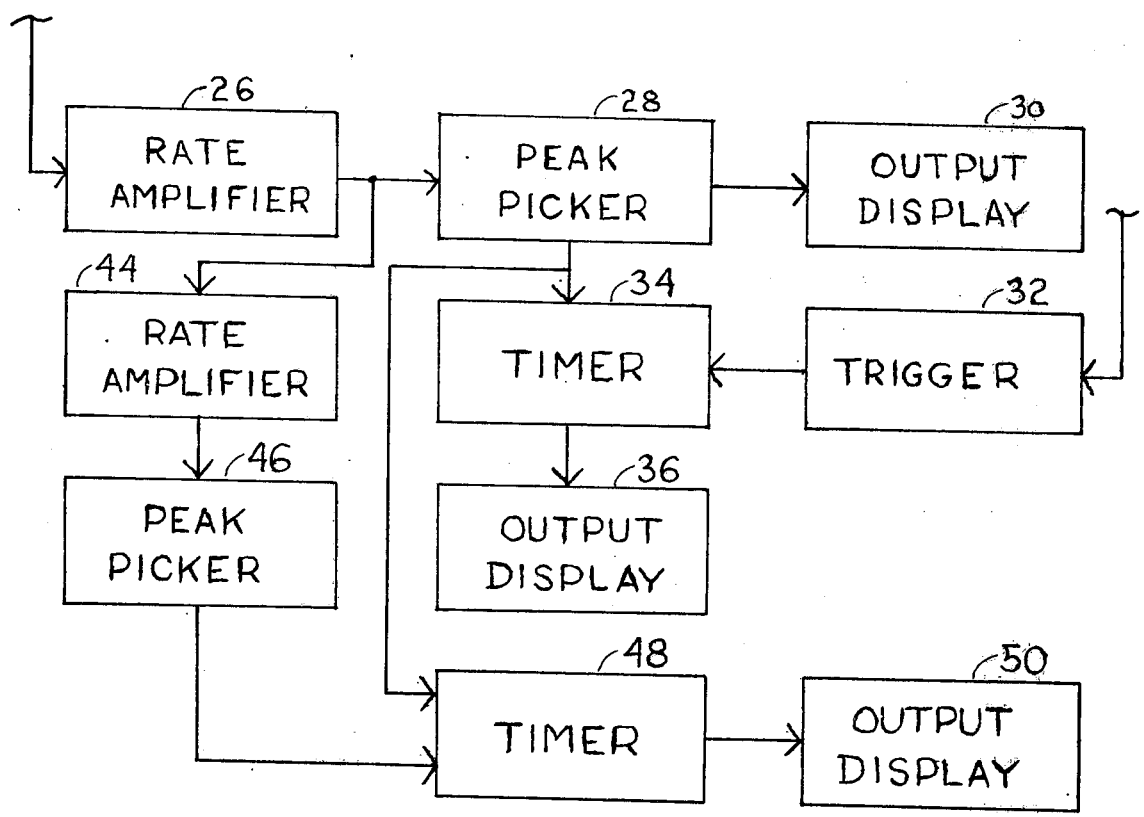
FIG. 21 is a block diagram of additional circuitry which may be added to the apparatus of FIG. 4 for practicing an alternate method of the present invention.

Additional circuitry which may be added to the apparatus of FIG. 4 to practice one of the methods of the present invention is shown in FIG. 21. Only that portion of the apparatus of FIG. 4 necessary to an understanding of the connecting of the additional circuitry is shown in FIG. 21. The purposes of the additional apparatus are the determination of the occurrence of a maximum in the second derivative of the nephelometric signal and the determination of the time duration between this maximum in the second derivative signal and the maximum in the first derivative signal. To this end, a second rate amplifier 44 is connected to the output of rate amplifier 26. Rate amplifier 26 provides an output signal which is a measure of the rate of change of the nephelometric signal with respect to time (the first derivative). When this signal is used as input to second rate amplifier 44, the output of amplifier 44 is a measure of the rate of change with respect to time of the first derivative of the nephelometric signal (the second derivative). Second rate amplifier 44 is connected to a second peak picker 46 which monitors the second derivative signal for a maximum. A second timer 48 is connected to both peak pickers 28 and 46. Timer 48 is started by peak picker 28 when a maximum is found in the first derivative of the nephelometric signal and stopped by peak picker 46 upon the occurrence of a maximum in the second derivative of the nephelometric signal. A second output display 50 is connected to timer 48 to display the elapsed time between maximums in the first and second derivatives of the nephelometric signal as computed by timer 48.

While the determination of the concentration of antibody/antigen from the single peak rate value is important, another important contribution of the present invention is the ability to determine antigen excess from the precise time of occurrence of the peak rate. It has been observed that the shape of the leading edge of the rate curve when the antibody/antigen reaction takes place in antibody excess is different from the leading edge of the rate curve which occurs when the reaction takes place in antigen excess. The further determination has been made that the precise time at which the peak rate occurs after the initiation of the antigen/antibody reaction can be used to indicate which of the two reaction constituents, antigen or antibody, is present in excess. Thus, in addition to measuring and recording the peak rate as a function of concentration, it is preferred that the precise time to the peak rate as a function of concentration be recorded as well.

Figure 7:
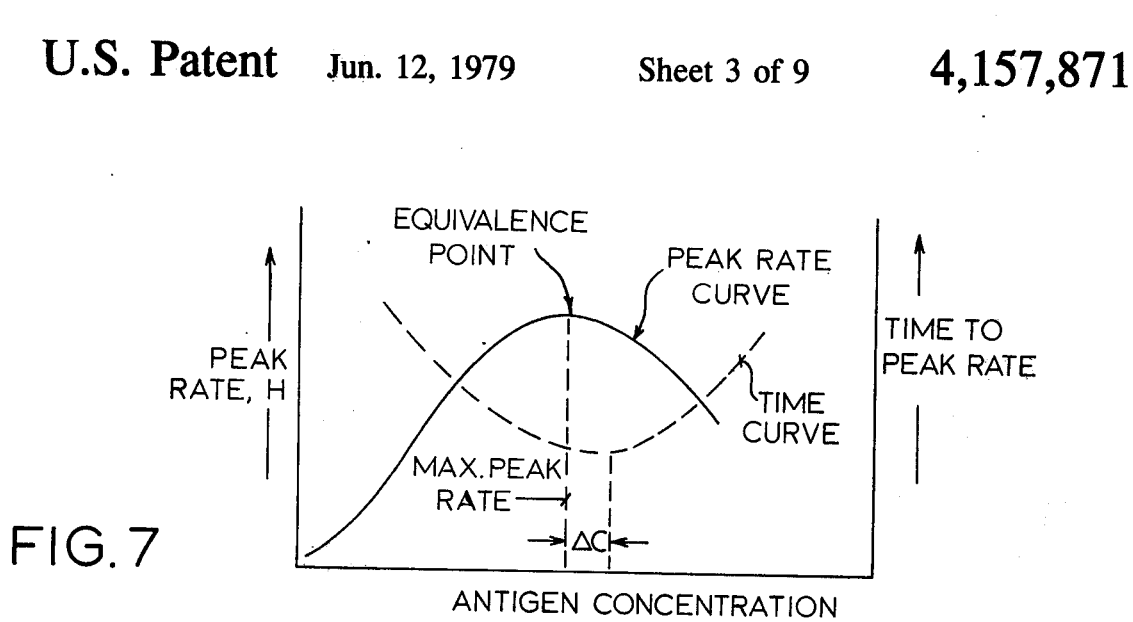
FIG. 7 is a graph of peak rates of the nephelometric signal superimposed on a graph of times to the peak rates during antigen/antibody quantification and excess determination, both as a function of antigen concentration.

FIG. 7 shows a graph of peak rate (H) vs. antigen concentration (C) for a given antibody concentration, as well as a superimposed graph of time to the peak rate (T) vs. concentration. Both curves tend to be parabolic about a region near antibody/antigen equivalence, with equivalence being defined as the center of symmetry of the peak rate curve, and the location of the maximum in the peak rate curve. The time curve is inverted with respect to the peak rate curve and has its minimum near the equivalence point of the peak rate curve. Although the minimum in the time curve may coincide with the maximum in the peak rate curve, in most cases it does not. It has been found that the relative position of the minimum of the time curve with respect to the equivalence point of the peak rate curve may be adjusted by altering the characteristics of the reagent solutions, for example ionic strength, ionic species, polyethylene glycol (PEG) concentration, etc. Defining $\Delta C$ as the difference in concentration units between the maximum in the peak rate curve and the minimum in the time curve, it can be seen that the two curves are inverted but symmetrical with respect to one another when $\Delta C$ equals zero. If $\Delta C$ is greater than zero, then the curves are asymmetric by an amount proportional to $\Delta C$.

Figure 8:
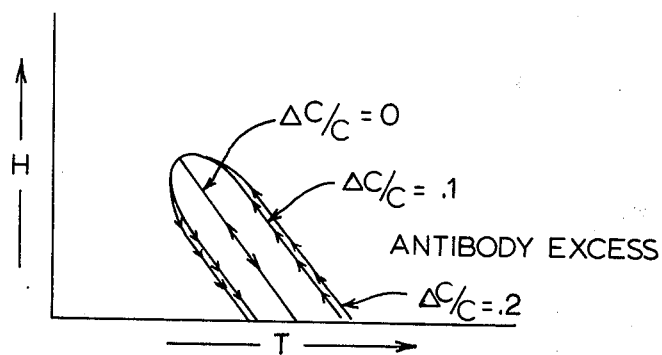
FIG. 8 is a graph of peak rate as a function of time to the peak rate for three conditions of $\Delta C/C$ (as defined in FIG. 7); $\Delta C/C = 0$, $\Delta C/C = 0.1$, and $\Delta C/C = 0.2$.

FIG. 8 is a plot of the peak rate (H) vs. the time to the peak rate (T) for the three values: $\Delta C/C = 0$, $\Delta C/C = 0.1$, and $\Delta C/C = 0.2$. The straight line representing the symmetric conditions, $\Delta C/C = 0$, is the locus of all points corresponding to a finite H and T. When some asymmetry occurs, so that $\Delta C/C$ takes on some positive value, the plot of H vs. T unfolds into the projection of a parabola on the HT plane, where the arrows indicate the direction of the H and T values along the line as concentration increases. In this case, concentrations corresponding to antibody excess are to the right of the straight line representing $\Delta C = 0$, and antigen excess corresponds to the lefthand side of the plot. If the asymmetry is to the opposite side so that $\Delta C$ takes on negative values, the minimum in T occurs before equivalence, and the results are the same as shown in FIG. 8 except that the arrows reverse direction, and antigen excess corresponds to the right side of the parabolic projection of H vs. T, while antibody excess corresponds to the lefthand side.

Since it is the object of the present invention to be able to establish antigen/antibody excess from a single determination of peak rate and time to that peak rate, it would be desirable if the time obtained could be compared to a single threshold value for purposes of making the antigen/antibody excess determination. As can be seen from FIG. 8, however, when H and T are graphed as a function of increasing concentration of antigen, no single value of time exists wherein the antibody excess portion of the curve is on one side of that value and the antigen excess portion of the curve is on the opposite side. Thus, the desired single value determination is impractical of implementation. To accomplish the objectives of the present invention, however, it has been found that it is possible to effect a coordinate transformation on the data of FIG. 8 in a manner which will establish a single value against which the test for antigen/antibody excess can be made.

Figure 9:
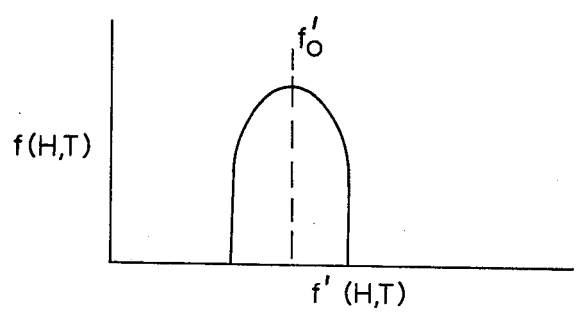
FIG. 9 is a graph of peak rate of the nephelometric signal as a function of time to the peak rate for a single value of $\Delta C/C \neq 0$ transformed to two new functional variables about new functional axes which will cause the maximum of the parabolic peak rate curve to occur about a vertical axis.

Referring to FIG. 9, H and T have been transformed into two new variables, f(H, T) and f'(H, T), such that if f'(H, T) is greater than some constant, f'$_0$, the solution is in antibody excess, and if f'(H, T) is less than f'$_0$, antigen excess applies. In the preferred embodiment of the present invention the coordinate transformation is effected as follows:

(1) Graph H vs. T as a nonvertical parabola from values for H and T generated by the reacting of antigen serum diluted with saline in an amount intended to be used as the calibration basis and at various known antigen concentration levels with the intended antibody plus any desired buffer solution. This graph will appear as in FIG. 8.

Figure 11:
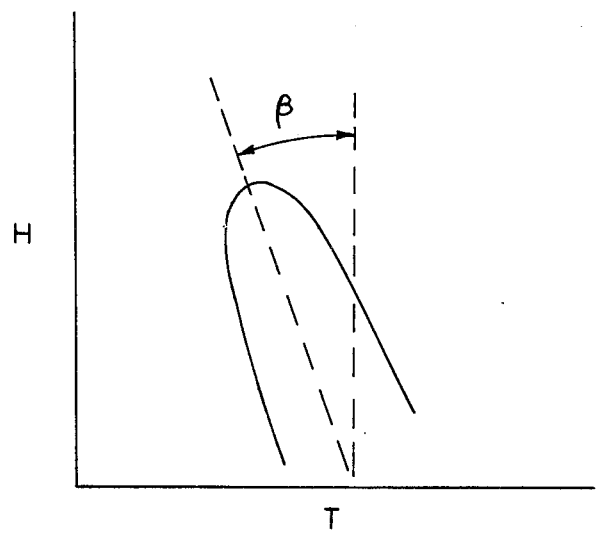
FIG. 11 is a graph of peak rate (H) of the nephelometric signal as a function of time (T) to the peak rate generated by a typical reaction of a specific protein in serum at a series of fixed dilutions in saline with its corresponding antibody reagent of known concentration in order to establish a calibration curve.

(2) Draw a line through the approximated parabola normal to the tangent at the vertex of the parabola as shown in FIG. 11. The line represents the rotation that must be effected as designated by angle $\beta = \tan^{-1} \Delta T/\Delta H$.

Figure 12:
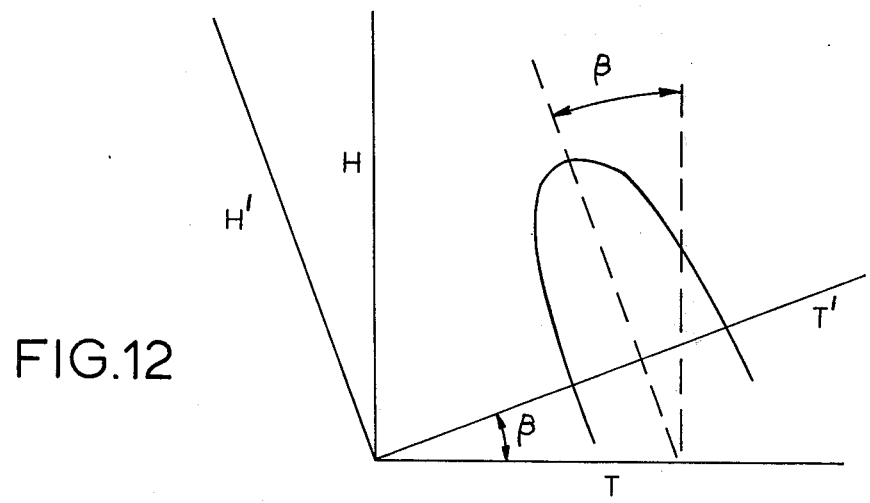
FIG. 12 is the graph of FIG. 11 having a second coordinate axis system (H',T') superimposed thereon in such a manner that an axis drawn through the parabola normal to the tangent at its vertex will also be normal to the T' axis.

(3) Rotate the H,T coordinate axes to the new positions H',T' so that the line of step (2) is normal to the T' axis as shown in FIG. 12.

(4) Find the new coordinates for the values of step (1) by the equations:

$$T' = T \cos \beta + H \sin \beta \qquad (13)$$

and, $$H' = T \sin \beta + H \cos \beta \qquad (14)$$

Figure 13:
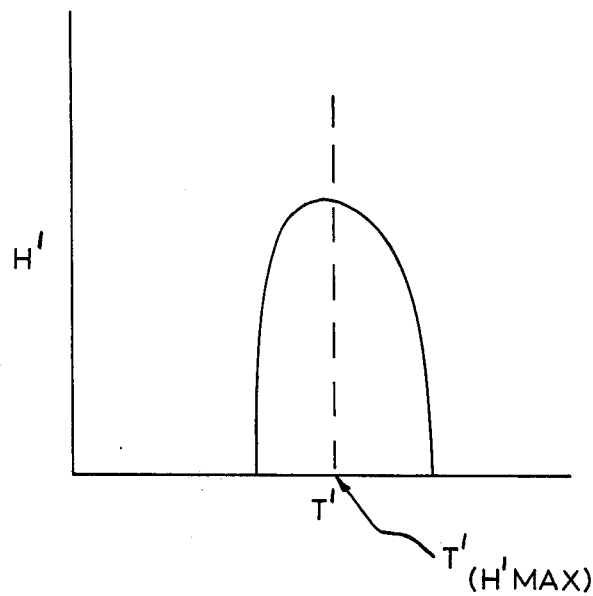
FIG. 13 is the H',T' axis system of FIG. 12 revolved to a vertical position and with the threshold value $T'_{(H'max)}$ of interest indicated.

The new coordinated values in T' and H' are then regraphed on the new H',T' coordinate system to give the parabola oriented 90° to the T' axis of FIG. 13.

(5) Determine the value of T' where H' is a maximum (the equilibrium point) to fix the threshold value. The equation for the parabola is:

$$H' = a + bT' + c(T')^2 \qquad (15)$$

for a maximum:

$$\frac{dH'}{dT'} = 0 = b + 2cT' \rightarrow T'_{(H'max)} = \frac{-b}{2c} \qquad (16)$$

Figure 14:
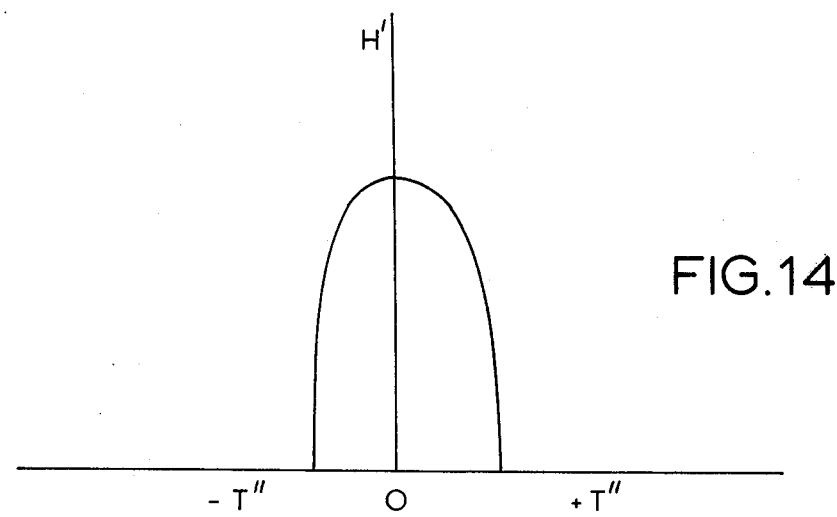
FIG. 14 is the H',T' axis system of FIG. 13 with the parabola shifted to cause the threshold value to occur at the zero value of the new coordinate system H',T''.

For ease of testing, the values $-b/2c$ can be subtracted from all T' values in order to translate the parabola to the origin so that zero is the threshold value. The new parabola representing the values of step (1) as transformed and graphed on a new H'T'' coordinate system is as shown in FIG. 14 and is of the form:

$$H' = a + bT'' + c(T'')^2 \qquad (17)$$

where, $$T'' = T' - (-\frac{b}{2c}) . \qquad (18)$$

(6) Determine antigen excess for any pair of values (H,T) by first transferring T to T' by equations (13) and (14) of step (4) and thence to T'' by subtracting the constant ($-b/2c$) developed in step (5). Antigen excess is then determined by whether T'' is greater than or less than zero, depending on the original parabola of H vs. T. For example, if the parabola of step (1) had antigen excess points on the left of the center line of the parabola, then antigen excess would be if T' is less than zero. These conditions are determined by the analyte and the buffer solutions as will be seen in the examples that follow.

Figure 15:
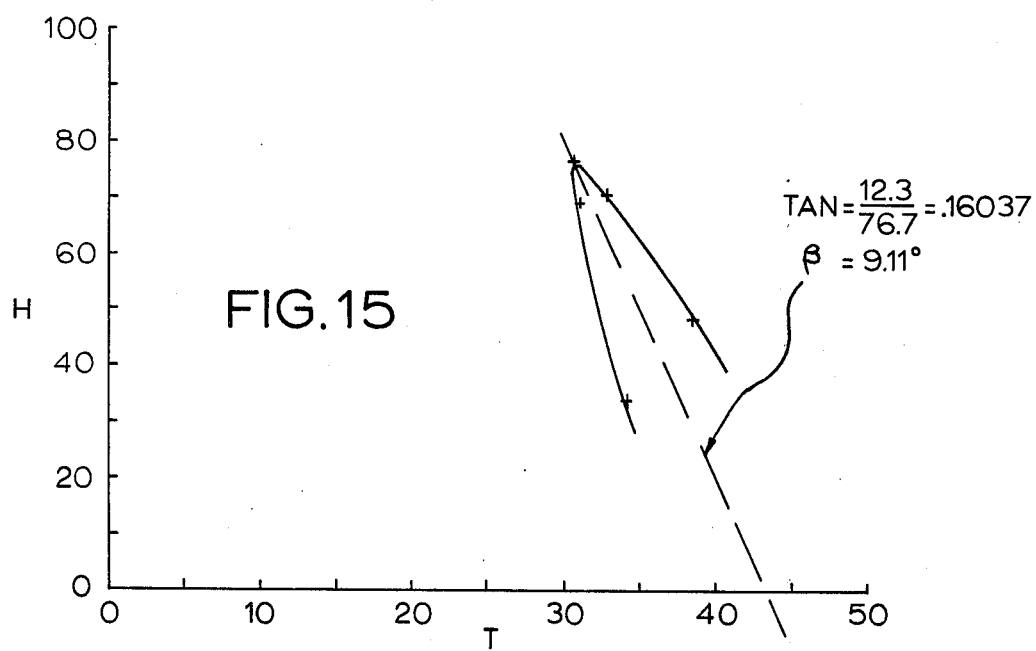
FIG. 15 is a graph of the form of FIG. 11 for the specific case of the third component of serum complement (C'3) diluted 1:6 in a buffer solution of 0.1 M NaCl+2% PEG.
Figure 16:
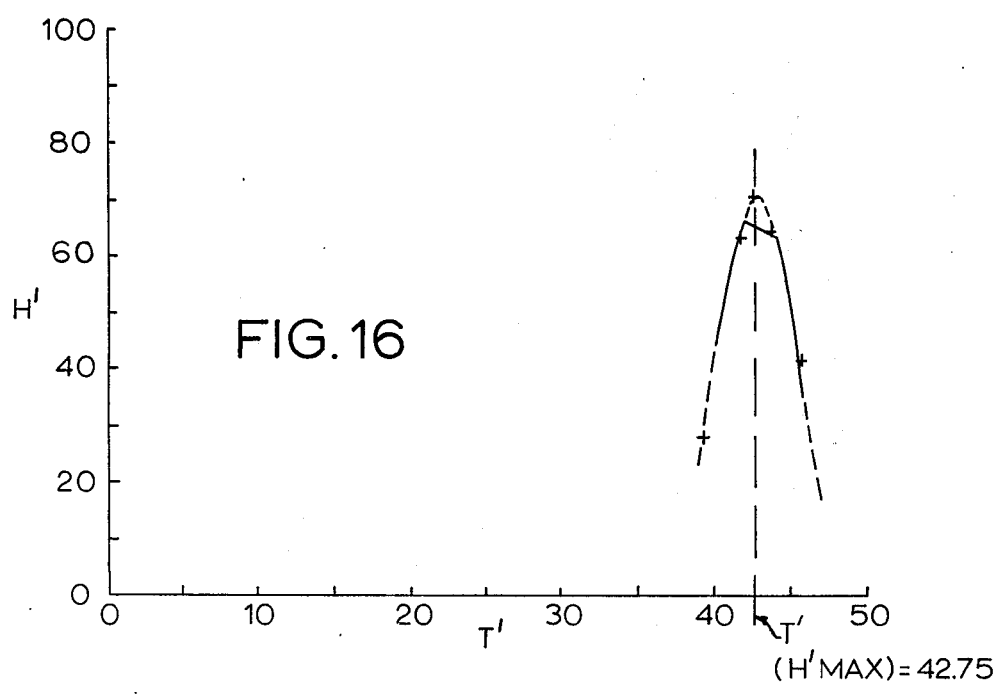
FIG. 16 is a graph of the form of FIG. 13 derived from FIG. 15.

EXAMPLE 1—See FIGS. 15 and 16—ANALYSIS of C'3

Calibration Conditions

Buffer—0.1 M NaCl+2% PEG
Antibody to C'3 diluted 1:6 in buffer

Calibration Data

| Sample | C'3 Concentration (g/l) | H | T | H' | T' | T'' |
|---|---|---|---|---|---|---|
| (190 1) | 6.384 | 34.0 | 34.2 | 28.16 | 39.15 | −3.60 |
| (#2) | 4.80 | 69.2 | 31.1 | 63.40 | 41.66 | −1.09 |
| (#3) | 3.22 | 76.7 | 30.7 | 70.87 | 42.46 | −0.29 |
| (#4) | 2.4 | 70.6 | 32.8 | 64.52 | 43.57 | +0.82 |
| (#5) | 1.6 | 48.5 | 38.5 | 41.79 | 45.69 | +2.94 |

CALCULATIONS $\tan = 12.3/76.7 - 0.16037$ $\beta = 9.11°$

T' at H' max = 42.75 therefore, $T'' = T' - 42.75$ so,

Antigen excess exists for T''<0

Example of Actual Test Serum Run Using Above Calibrated Conditions:

| C'3 Concentration (g/l)(calculated) | H | T | T' | T'' |
|---|---|---|---|---|
| .96 | 18.8 | 58.7 | 60.94 | 18.19 |

CONCLUSION:

This sample which shows a T''>0 is in antibody excess.

EXAMPLE 2—See FIGS. 17 and 18—ANALYSIS of IgG

Calibration Conditions

Buffer—0.1 M NaCl+3% PEG
Antibody to IgG diluted 1:8 in buffer

Calibration Data

| Sample | IqG Concentration (g/l) | H | T | H' | T' | T" |
|---|---|---|---|---|---|---|
| (#1) | 25.00 | 37.1 | 37.6 | 35.73 | 46.20 | 3.04 |
| (#2) | 20.00 | 49.7 | 33.6 | 38.82 | 45.74 | 2.58 |
| (#3) | 16.67 | 61.1 | 25.3 | 52.03 | 40.82 | −2.34 |
| (#4)* | 14.29 | 62.0 | 27.5 | 52.31 | 43.18 | 0.02 |
| (#5) | 12.50 | 59.0 | 27.5 | 49.42 | 42.37 | −0.79 |
| (#6) | 10.00 | 50.9 | 27.7 | 41.56 | 40.30 | −2.78 |
| (#7) | 5.00 | 22.0 | 34.6 | 11.87 | 39.25 | −3.91 |

*note discussion relative to erratic behavior of the ne phelometric signal near equivalence that follows

CALCULATIONS $\tan = 16.5/59.0 = 0.27966$ $\beta = 15.62°$ $T$ at $H'$ max $= 43.16$ therefore, $T' = T - 43.16$ so, Antigen excess exists for $T'' > 0$ Examples of Actual Test Serum Run Under Above Calibration Conditions:

Data

| | IqG Concentration (g/l)(calculated) | H | T | T' | T" |
|---|---|---|---|---|---|
| #1 | 33.33 | 115 | 56.8 | 57.79 | 14.63 |
| #2 | 3.75 | 141 | 39.6 | 41.93 | −2.23 |

CONCLUSIONS

1 is in antigen excess and #2 is in antibody excess.

The present invention is based on the discovery that the portion of the rate curve of the nephelometric signal from the moment of initiation of the reaction up to the point of the peak rate has characteristics which can be related to the value of the peak rate and the time to the peak rate in a manner which will allow the curve occurring in antigen excess to be distinguished from the curve existing in antibody excess. The foregoing coordinate transformation technique is only one of the techniques developed for implementing an imunonephelometric analysis based on this discovery. It is to be understood that the essence of the present invention is the identification of antigen/antibody excess through the analysis of that portion of the rate curve existing between the initiation of the reaction and the occurrence of the peak rate. Numerous means can be employed for implementing the described decision making techniques for the present invention which means form no part of the present invention. For example, the displayed values derived from the nephelometric apparatus described above can be used for hand calculation. Electronic circuitry can be employed. In the preferred embodiment, it has been found most advantageous to employ a digital computer connected to the signal outputs whereby the values of H and T can be sensed and the required calculations performed by the computer.

Figure 10:
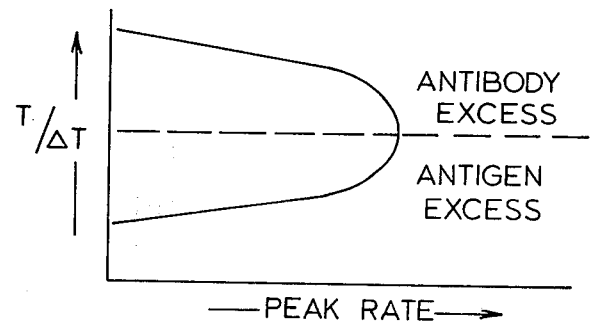
FIG. 10 is a graph of $T/\Delta T$ as a function of peak rate of the nephelometric signal where T is the time to the peak rate and $\Delta T$ is the difference in time between the peak rate and the peak rate of the second derivative of the nephelometric signal during antigen/antibody quantification and excess determination.

A second technique which can be employed in the analysis of the indicated portion of the rate curve whereby antibody/antigen excess can be determined, is shown in relation to FIG. 10. This technique requires the addition of circuitry to the system capable of providing the second derivative of the nephelometric signal, that is, the rate of change of the rate curve with respect to time. In this technique, the elapsed time to the first derivative is modified to a new test value as a function of a second variable. In this case the second variable is the second derivative of the nephelometric signal. Referring to FIG. 10, a plot of $T/\Delta T$ (where T is the time to the peak rate of the first derivative, and $\Delta T$ is the difference in time between the peak rate of the first derivative and the peak of the second derivative signal) is shown as a function of the peak rate. As can be seen from FIG. 10, the shape difference in the rate curve between antibody excess and antigen excess exhibits itself as a change in the test value $T/\Delta T$ such that if $T/\Delta T$ is above some fixed level, antibody excess applies, while if $T/\Delta T$ is below that level antigen excess applies. It is to be noted, that by employing this latter technique, the value of the peak rate (H) does not enter into the determination of antigen/antibody excess as in the foregoing coordinate transformation technique. In the latter second derivative technique, antibody/antigen excess becomes a function of time alone. As with the first derivative only technique, calibration is first accomplished to determine the threshold value under known fixed conditions. Once established, the threshold value can be used to determine antibody/antigen excess in test sera reacted under the same fixed conditions.

Figure 19:
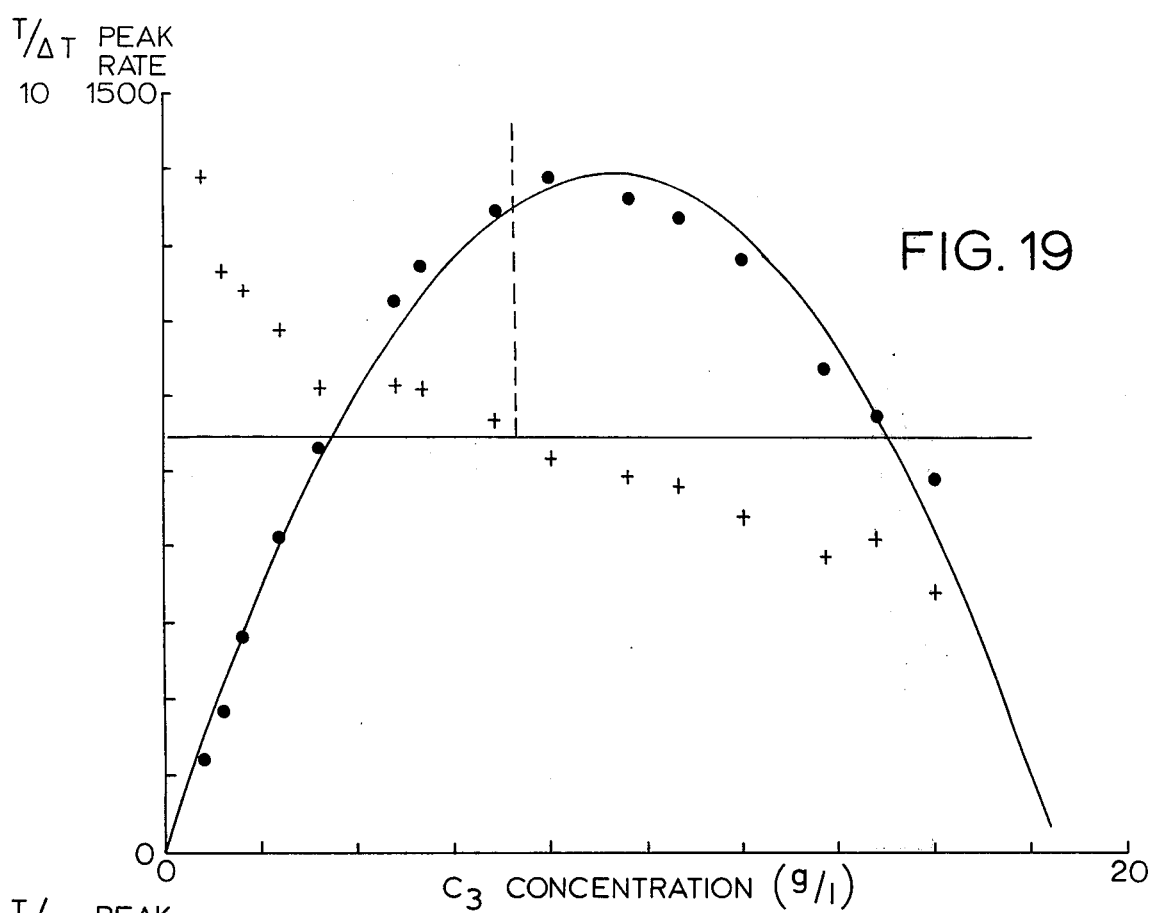
FIG. 19 is a graph of peak rate of the nephelometric signal as a function of concentration of antigen with corresponding values of $T/\Delta T$ (as defined with respect to FIG. 10) superimposed thereon. The threshold value for indicating antibody excess is indicated by the horizontal line through the curve near equilibrium. The graph is for C'3 diluted 1:4 in a buffer of 0.1 M NaCl+4% PEG.

A first example of the calibration technique for C'3 is shown with reference to FIG. 19. In this instance, C'3 antibody was contained in 0.1 M NaCl+4% Polyethylene Glycol (PEG) buffer. The antibody dilution in saline was 1:4. The peak rates of the nephelometric signal observed at various C'3 concentrations are represented by the large "dots" through which the peak rate curve has been fit. This is easily accomplished (as was done in this case) through the use of a computer program and X-Y plotter into which the displayed values were input and which is adapted to perform such graphic and curve fitting functions. The value of $T/\Delta T$ calculated from the displayed values of T and $\Delta T$ for each peak rate point is designated by a "+" corresponding vertically with the "dot". As can be seen in FIG. 19, as the value of $T/\Delta T$ decreases, the C'3 concentration goes from antibody excess, through equilibrium, into antigen excess. It is characteristic of such nephelometric analysis that the readings obtained about equilibrium are unreliable (see, for example, data 3, 4 and 5 under Example 2 above). Thus, when quantizing antigens in sera, it is desirable to eliminate not only those readings clearly in antigen excess, but those in equilibrium as well. A value is thus chosen as the threshold or test point of test value $T/\Delta T$ such as that represented by the horizontal line at $T/\Delta T = 5.2$ which has a projected peak rate value associated with it which is far enough down on the antibody excess portion of the curve whereby if the value of $T/\Delta T$ is greater than the threshold value the solution is clearly in antibody excess. In use later, this value can be adjusted slightly higher if occasional erratic readings close to the threshond value indicate the threshold value is still allowing supposedly valid results too close to the equilibrium portion of the curve.

Figure 20:
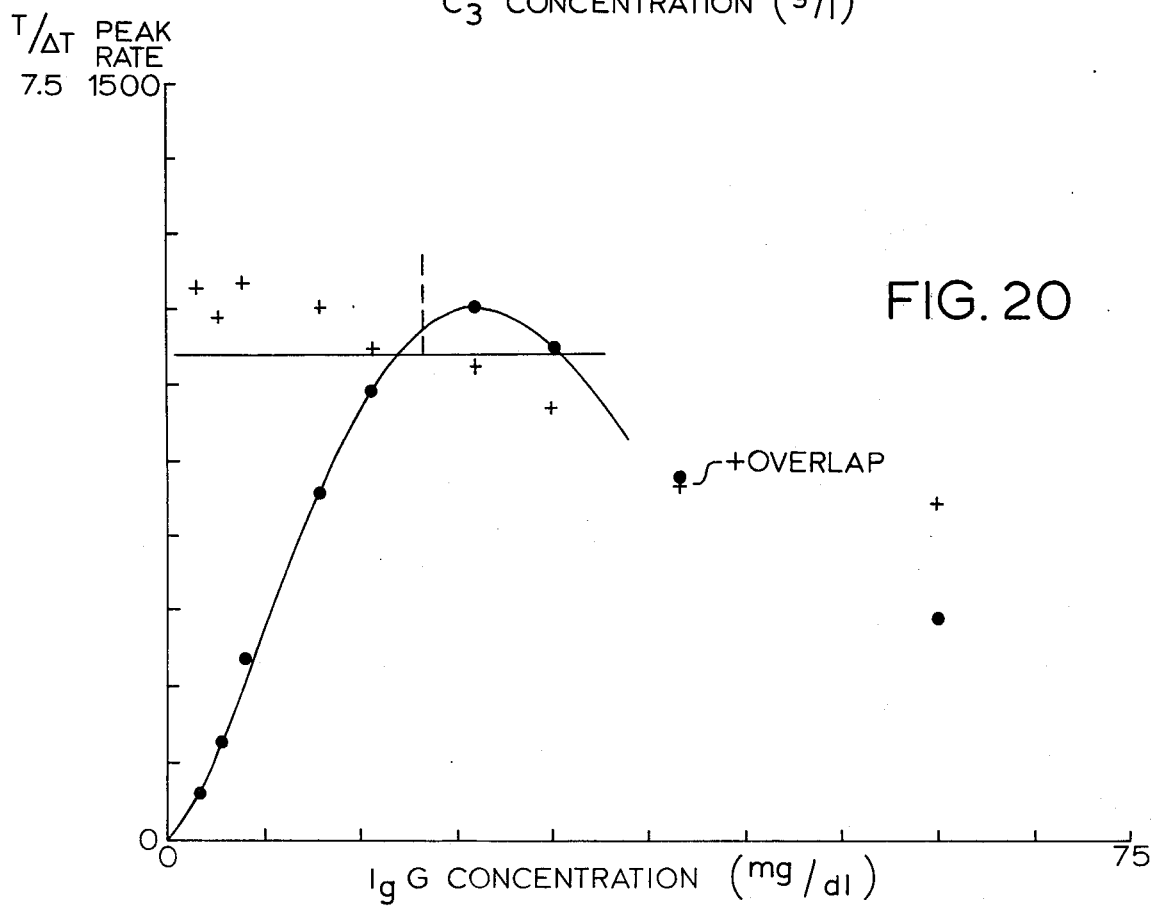
FIG. 20 is a graph such as that of FIG. 19 for IgG diluted 1:5 in a buffer solution of 0.15 M NaCl+4% PEG.

A second example of calibration to fix the threshold value is shown in FIG. 20 employing IgG in 0.15 M NaCl+4% PEG buffer. The antibody dilution in saline was 1:5. Again, the peak rate points of the nephelometric signal occurring at observations taken at various antigen concentrations are shown by the large "dots" while the calculated T/ΔT values are indicated by the "+" associated vertically with each "dot". The curve-fit computer program was unable to fit an acceptable parabola to the peak rate values because of the excessive "tail-off" of the points at the higher antigen concentration levels. The portion of the parabola of interest, however, as drawn through the points by hand, is clearly visible, allowing a threshold value of 4.6 to be easily established. Thus, when testing serum, if the test value T/ΔT is greater than 4.6 the solution is in antibody excess. Correspondingly, a T/ΔT value less than 4.6 indicates an unacceptable concentration value since the solution is either in the equilibrium region or in antigen excess.

It is to be understood that while the test value of T/ΔT is used as a preferred function of time in the preceding examples, the requirement of the function of time used as a test value need only be such as to create a constantly ascending or descending value as the concentration of the antigen increases. Test values such as 2T/ΔT, T/ΔT+2, etc., may be acceptable and used while still employing the present invention.

Thus, in employing the methods of the present invention for determining antigen-antibody excess during immunoassay employing true rate techniques, it can be seen that a threshold value must be established. This is accomplished by observing the behavior of the nephelometric signal from antigen-antibody reactions taking place under known, fixed conditions. This threshold value can then be used to test the data from test serum run under the same fixed conditions. Everything in the reaction of the test serum is known except the concentration of antigen and the status of antigen-antibody excess. By comparison to the threshold value previously established according to the foregoing techniques, the peak rate data observed in the nephelometric signal from the test serum can be used to determine the antigen-antibody excess state of the test serum used in the reaction.

Having thus described our invention, we claim:

1. Immunonephelometric analysis apparatus comprising:
   (a) a cell for holding a sample containing precipitin-forming antigen or antibody;
   (b) means for producing and directing a light beam into a sample in said cell;
   (c) photodetector means for detecting scattered light from said sample and for producing a signal indicative of the quantity thereof;
   (d) first signal differentiator means connected to said photodetector means for producing a first rate signal indicative of the rate of change with respect to time of said quantity of scattered light;
   (e) first peak rate detector means connected to said first signal differentiator means for detecting a maximum value of said first rate signal; and,
   (f) trigger means for producing a start signal upon initiation of an immunochemical reaction in said cell.

2. The immunonephelometric analysis apparatus of claim 1 additionally comprising:
   first timer means connected to said first peak rate detector means and to said trigger means for determining the elapsed time between the initiation of said immunochemical reaction and the occurrence of said maximum in said first rate signal.

3. The immunonephelometric analysis apparatus of claim 1 additionally comprising:
   means for displaying a signal indicative of said maximum value to an operator using the apparatus.

4. The immunonephelometric analysis apparatus of claim 2 additionally comprising:
   means for displaying a signal indicative of said elapsed time to an operator using the apparatus.

5. The analysis apparatus of claim 1 additionally comprising:
   signal conditioner means for removing unipolar noise from said light scatter signal disposed between said photodetector means and said first signal differentiator means.

6. The analysis apparatus of claim 2 additionally comprising:
   (a) second signal differentiator means connected to said first signal differentiator means for producing a second rate signal indicative of the rate of change with respect to time of said first rate signal;
   (b) second peak rate detector means connected to said second signal differentiator means for detecting a maximum value of said second rate signal; and,
   (c) second timer means connected to said first and second peak rate detector means for determining the elapsed time between the occurrence of said maximum in said second rate signal and the occurrence of said maximum in said first rate signal.

7. A method of determining antigen/antibody excess in immunonephelometric analysis comprising the steps of:
   (a) passing a beam of light into a sample cell wherein an antibody/antigen reaction is taking place;
   (b) sensing the start of the reaction;
   (c) measuring the intensity of a nephelometric signal produced by said light beam scattering from an antigen/antibody precipitate forming from the reaction;
   (d) producing a first time derivative signal from said nephelometric signal;
   (e) detecting a maximum value H of said first derivative signal; and,
   (f) comparing a function f(H) of said maximum value (H) graphable on a first coordinate system to a first threshold value whereby if said f(H) is on one side of said first threshold value antigen excess is determined and if said f(H) is on the other side of said first threshold value antibody excess is determined.

8. The method of claim 7 additionally including the step of:
   continuously stirring the contents of the sample cell during steps (a) through (e).

9. The method of claim 7 wherein said f(H) is the elapsed time T from the start of the reaction until H is detected.

10. The method of claim 9 including the additional steps of:
    performing a coordinate transformation into a second coordinate system on said elapsed time T as a function of said maximum value H and adjusting said first threshold value to a second threshold value in said second coordinate system before said step of comparing said elapsed time to said threshold value.

11. The method of claim 10 wherein said step of performing a coordinate transformation into a second coordinate system comprises the steps of:
   (a) graphing H v. T as a nonvertical parabola on an H,T coordinate system from values for H and T generated by the reacting of antigen containing sample diluted in an amount intended to be used as a calibration basis and at various known antigen concentration levels with the intended antibody solution plus any desired buffer;
   (b) drawing a line through said parabola normal to a tangent at a vertex of said parabola, said line representing a rotation that must be effected to normalize said parabola as designated by an angle $\beta = \tan^{-1} \Delta T/\Delta H$;
   (c) rotating the H,T coordinate axes to new positions H',T' to form a H',T' coordinate system so that said line of step (b) is normal to the T' axis;
   (d) finding new coordinates for the values of step (a) by the equations:

$$T' = T \cos \beta + H \sin \beta \qquad (d1)$$

and $$H' = T \sin \beta + H \cos \beta; \qquad (d2)$$

(e) regraphing said new coordinated values in T' and H' on said new H',T' coordinate system to give a parabola oriented 90° to the T' axis of said new H',T' coordinate system;
   (f) determining the value of T' where H' is a maximum (the equilibrium point) to fix said second threshold value, the equation for the parabola being $$H' = a + bT' + c(T')^2 \qquad (f1)$$

wherefore, for said maximum $$\frac{dH'}{dT'} = 0 = b + 2cT' \rightarrow T'_{(H'max)} = \frac{-b}{2c}; \text{ and,} \qquad (f2)$$

(g) determining antigen/antibody excess for any pair of values (H,T) obtained in immunonephelometric analysis of an antigen/antibody reaction by first transferring T to T' by equation (d1) of step (d) above and then comparing the value of T' to said threshold value of equation (f2) of step (f) above whereby antigen/antibody excess is determined.

12. The method of claim 9 including the additional steps of:
   (a) producing a second time derivative signal from said nephelometric signal as being the time rate of change of said first time derivative signal;
   (b) detecting a maximum value of said second derivative signal;
   (c) determining the elapsed time between the occurrence of said maximum value of said second derivative signal and the occurrence of said maximum value of said first derivative signal; and,
   (d) modifying the value of said elapsed time from the start of the reaction to the occurrence of said maximum value of said first derivative signal as a function of said elapsed time between the occurrence of said maximum value of said second derivative and the occurrence of said maximum value of said first derivative before said step of comparing said elapsed time to said first threshold value.

13. The method of claim 12 wherein:
   said step of modifying is accomplished by dividing said elapsed time from the start of the reaction to the occurrence of said maximum value of said first derivative signal by a value proportional to said elapsed time between the occurrence of said maximum value of said second derivative and the occurrence of said maximum value of said first derivative.

14. In a method of immunonephelometric analysis, the steps of:
   (a) passing a beam of light into a smaple cell where an antibody/antigen reaction is occurring;
   (b) monitoring light scattering from a precipitate forming from the reaction to develop a nephelometric signal;
   (c) differentiating the nephelometric signal to develop a rate signal the peak value of which is a measure of a quality of a reactant in the reaction; and
   (d) determining whether the reaction is proceeding in an antigen or antibody excess condition.

15. The method of claim 14 wherein step (d) comprises:
   comparing a function of the peak value of the rate signal with a predetermined threshold value for the function indicative of a threshold for excess of antigen in the particular antibody/antigen reaction being monitored to determine whether the reaction is proceeding in an antigen or antibody excess condition.

16. The method of claim 15 including the step of pre-establishing the threshold value for the function indicative of a threshold for excess of antigen in the particular antibody/antigen reaction being monitored.

17. The method of claim 15 further including the steps of:
   (e) sensing the start of the reaction, and
   (f) measuring the elapsed time (T) from the start of the reaction until the peak value is reached, and
   wherein the function of the peak value is the elapsed time.

18. The method of claim 17 further including the steps of:
   (g) detecting the occurrence of a maximum peak in the rate signal;
   (h) producing a second time derivative signal from the nephelometric signal;
   (i) detecting a maximum value of the second derivative signal;
   (j) measuring the elapsed time ($\Delta T$) between the occurrence of the maximum value of the second derivative signal and the occurrence of the maximum peak in the rate signal;
   wherein the comparison operation of step (d) comprises a comparison of a function of T and $\Delta T$ with a predetermined value of the function to determine whether the reaction is proceeding in an antigen or antibody excess condition.

19. The method of claim 15 including the step of:
   establishing said predetermined threshold value at a level discriminating between a peak value which is clearly in one of an antigen or antibody excess condition and a peak value which is either in equilibrium or in the other one of said antigen or antibody excess condition.

* * * * *